United States Patent
Semary

(10) Patent No.: US 11,930,824 B1
(45) Date of Patent: Mar. 19, 2024

(54) MARINE ALGAE FOR INSECT BIOCONTROL

(71) Applicant: KING FAISAL UNIVERSITY, Al-Ahsa (SA)

(72) Inventor: Nermin Adel El Semary, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/124,877

(22) Filed: Mar. 22, 2023

(51) Int. Cl.
| | |
|---|---|
| C12N 1/06 | (2006.01) |
| A01N 65/03 | (2009.01) |
| A01P 7/04 | (2006.01) |
| C05F 11/02 | (2006.01) |
| C12P 1/00 | (2006.01) |
| C12P 5/00 | (2006.01) |

(52) U.S. Cl.
CPC ............... *A01N 65/03* (2013.01); *A01P 7/04* (2021.08); *C05F 11/02* (2013.01); *C12N 1/066* (2013.01); *C12P 1/00* (2013.01); *C12P 5/007* (2013.01)

(58) Field of Classification Search
CPC . C12N 1/066; C12P 1/00; C12P 5/007; A01N 65/03; A01N 65/00
See application file for complete search history.

(56) References Cited

PUBLICATIONS

Jeliani et al., Journal of the Marine Biological Association of the United Kingdom, 2021, 101: 527-534 (Year: 2021).*
Aroyehun et al., Molecules, 2019, 24:3298, pp. 1-23 (Year: 2019).*
January et al., Algal Research, 2019, 40:101517, pp. 1-8 (Year: 2019).*
Cystoseira muricata, downloaded on Aug. 18, 2023 from the website of WoRMS—World Register of Marine Species, https://www.marinespecies.org/aphia.php?p=taxdetails&id=500123 (Year: 2023).*
Papanfuss et al., BLUMEA, vol. XV, No. i, 1967, pp. 17-24 (Year: 1967).*
Haleem et al., "Screening and evaluation of different algal extracts and prospects for controlling the disease vector mosquito *Culex pipiens* L." Saudi Journal of Biological Sciences vol. 29, Issue 2, Feb. 2022, pp. 933-940.
Yu et al., "2,4-Dichlorophenoxyacetic acid (2,4-D) adsorptive removal by algal magnetic activated carbon nanocomposite," Chemosphere vol. 310, Jan. 2023, 136883.
Rashwan et al., "Toxic effect of Spirulina platensis and Sargassum vulgar as natural pesticides on survival and biological characteristics of cotton leaf worm *Spodoptera littoralis*," Scientific African, vol. 8, Jul. 2020.
Fouda et al., "Enhanced Antimicrobial, Cytotoxicity, Larvicidal, and Repellence Activities of Brown Algae, Cystoseira crinita-Mediated Green Synthesis of Magnesium Oxide Nanoparticles," Front Bioeng Biotechnol., Published online Feb. 28, 2022.
Boutjagoualt et al., "Chemical composition and insecticidal effects of brown algae (*Fucus spiralis*) essential oil against Ceratitis capitata Wiedemann (Diptera: Tephritidae) pupae and adults," Biocatalysis and Agricultural Biotechnology 40 (1), Feb. 2022.

* cited by examiner

*Primary Examiner* — Allison M Fox
*Assistant Examiner* — Qing Xu
(74) *Attorney, Agent, or Firm* — Nath, Goldberg & Meyer; Richard C. Litman

(57) ABSTRACT

The present algae extracts are used for biocontrol of insects. Specifically, the present extracts are obtained from *Cystoseria muricatum* using a polysolvent system. Once obtained, the extracts can be applied to plants to repel insects and/or to facilitate fertilization of the plants.

4 Claims, No Drawings

MARINE ALGAE FOR INSECT BIOCONTROL

BACKGROUND

1. Field

The disclosure of the present patent application relates to algae extracts, and particularly to algae extracts used for insect biocontrol.

2. Description of the Related Art

The ever-increasing threat from infectious diseases and the development of insecticide resistance in mosquito populations drives the global search for new natural insecticides. Mosquitoes act as vectors of pathogens and parasites that cause dreadful diseases (malaria, lymphatic filariasis, dengue, chikungunya, yellow fever, Zika virus and Japanese encephalitis). To control mosquito borne diseases, traditional chemical insecticides have been developed in the last 30 years. However, such chemical insecticides typically cause undesirable consequences in human beings and thus affect the ecosystem causing negative impact on non-target organisms (human and beneficial organisms and insects). In addition to the development of insect resistance, contamination of natural resources can have an impact on the food chain and reduce biodiversity.

Continual application of synthetic insecticides in controlling mosquito larvae has resulted in several problems, as build-up of mosquito resistance has had negative impacts on human health and environment, as such harmful chemicals and insecticides typically represent an environmental hazard and a threat to public health. Discovering new and affordable bio-insecticidal agents with high efficiency, cost effectiveness and that are target specific has become a crucial need.

Therefore, researchers have recently focused on novel and potentially eco-friendly control tools. Algae are a group of photosynthetic organisms which inhabit a wide range of environments. Although most algae are nutritious food for mosquito larvae, some species kill the larvae when ingested in large quantities, while others can repel mosquitos, as well as other insects. The development of bioinsecticides such as algal extracts represent safe, applicable, and low-cost alternatives for synthetic pesticides, which negatively affect the environment and health. They can contain several active compounds with potential biopesticidal activity for pest control and contributing to sustainable agriculture.

The larvicidal and repellant activity of various algae extracts have been studied, for example, red and green algal extracts such as those from *Galaxaura elongata*, *Jania rubens*, *Codium tomentosum*, *Ulva intestinales*, *Padina boryana*, *Dictyota dichotoma*, *Sargassum dentifolium* (Phaeophyta), and *Gelidium latifolium* (Rhodophyta). Blue and brown algal extracts, such as from *Spirulina platensis* and *Sargassaum vulgar*, have been studied as well. However, none of these algae extracts, to date, have shown significant effects in repelling insects from crops or plants.

Thus, new algae extracts useful as insect repellants when applied to plants solving the aforementioned problems are desired.

SUMMARY

In certain embodiments, the present subject matter relates to new algae extracts, processes for obtaining the same, and methods of using the same for repelling insects and for fertilizing various plants.

In one embodiment, the present subject matter relates to a process for preparing an algae extract, the process comprising: homogenizing a *Cystoseira muricata* biomass with a polysolvent system to obtain a homogenized mixture; maintaining the homogenized mixture in a closed environment for a period of time to allow extraction of bioactive compounds therefrom; separating the bioactive compounds; and collecting the separated compounds to obtain the algae extract.

In another embodiment, the present subject matter relates to an algae extract of *Cystoseira muricata* prepared by the processes described herein.

In a further embodiment, the present subject matter relates to methods of repelling insects from plants, as well as methods of fertilizing plants, comprising applying the *Cystoseira muricata* extract to said plants.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In one embodiment, the present subject matter relates to a process for preparing an algae extract, the process comprising: homogenizing a *Cystoseira muricata* biomass with a polysolvent system to obtain a homogenized mixture; maintaining the homogenized mixture in a closed environment for a period of time to allow extraction of bioactive compounds therefrom; separating the bioactive compounds; and collecting the separated compounds to obtain the algae extract.

In one embodiment, the polysolvent system used in the present process comprises water, methanol, and chloroform. In another embodiment in this regard, the polysolvent system comprises water, methanol, and chloroform in an about 1:1:1 ratio, v:v:v. The amounts of each solvent used is less critical than maintaining the equal ratio of the various solvents on a volume basis. That is, large amounts of the solvents as well as small amounts of the solvents may each be effective. Further, in an embodiment, the solvents used in the polysolvent system will have varying polarities to allow maximum extraction of a variety of materials from the *Cystoseira muricata* biomass having varying affinities and polarities.

In another embodiment, the homogenized mixture is maintained in a closed environment for a period of time that can be one or more days. In certain embodiments, the period of time is at least one, at least two, at least three, at least four, or at least five days. In one embodiment, the period of time is at least three days. The period of time will be that amount of time sufficient to cause the algae bioactive material to be thoroughly extracted from the biomass.

In a further embodiment, the separating step can be conducted by centrifuging the homogenized mixture containing the bioactive compounds. Other separation procedures known to those of ordinary skill in the art can be used as well.

In yet another embodiment, the present process can further comprise air drying the algae extract after it has been separated. Air drying the algae extract as this final step can help achieve absolute or maximum concentration of the algae extract.

In certain embodiments, the present subject matter relates to an algae extract of *Cystoseira muricata* prepared by the processes described herein. In this regard, the *Cystoseira muricata* is known as a brown algae. As such, it is expected that the *Cystoseira muricata* extract as prepared herein will include bioactive compounds typical to brown algae including, by way of non-limiting example, bioactive compounds selected from the group consisting of tannins, terpenes, flavonoids, and saponins. Most if not all these bioactive components can have a certain level of insect repellant activity.

In further embodiments in this regard, the concentration of each of these bioactive compounds in the produced algae extract can vary according to the age of the algae, metabolic activity, and ecological adaptation.

In one embodiment, the present subject matter further relates to methods of repelling insects from plants, as well as methods of fertilizing plants, comprising applying the *Cystoseira muricata* extract to said plants. In certain embodiments in this regard, the extract can be diluted with water prior to application to the plants. In alternative embodiments, the extract can be concentrated prior to application to the plants. In additional embodiments, the extracts can be applied to date palm trees to repel insects from the date palm trees, and/or to fertilize the date palm trees.

In further embodiments, various insects can be repelled from the plants after application of the present extracts. In one embodiment in this regard, the insects that can be repelled are flies. Other insects, including, by way of non-limiting example, mosquitoes and the like, can be similarly repelled from the plants treated with the present extracts. Regardless of the specific type of insect, after application to the plants, the extract deters said insects from approaching said plants.

EXAMPLES

Example 1

100 gm of fresh *Cystoseira muricata* biomass was homogenized with 450 ml of polysolvent system (water; methanol:chloroform; 1:1:1) (v/v/v). The mixture was homogenised and maintained in a closed jar for three days to allow extraction of bioactive compounds. The mixture was then centrifuged and the supernatant was collected. The mixture was left to concentrate and evaporate solvents. 15 ml of the residue was then diluted to 100 ml with water and used as an insect repellent.

It is to be understood that the algae extracts are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A process for preparing an algae extract, the process comprising:
   homogenizing a *Cystoseira muricata* biomass with a polysolvent system to obtain a homogenized mixture, wherein the polysolvent system contains water, methanol, and chloroform at a volume ratio of about 1:1:1;
   maintaining the homogenized mixture in a closed environment for a period of time to allow extraction of bioactive compounds therefrom;
   separating the bioactive compounds; and
   collecting the separated compounds to obtain the algae extract.

2. The process as recited in claim 1, wherein the period of time is at least three days.

3. The process as recited in claim 1, wherein the separating step is conducted by centrifuging the homogenized mixture containing the bioactive compounds.

4. The process as recited in claim 1, further comprising air drying the algae extract.

\* \* \* \* \*